(12) United States Patent
Grimard

(10) Patent No.: US 8,293,045 B2
(45) Date of Patent: Oct. 23, 2012

(54) METHOD TO INTEGRATE AN RFID COMPONENT IN A PROSTHESIS OR IMPLANT SUBSTITUTE OR IN A SURGICAL INSTRUMENT IN POLYMER OR PLASTIC

(75) Inventor: Jean-Christophe Grimard, Cellettes (FR)

(73) Assignee: Sferic Stellite, Menars (FR)

( * ) Notice: Subject to any disclaimer, the term of this patent is extended or adjusted under 35 U.S.C. 154(b) by 182 days.

(21) Appl. No.: 12/831,543

(22) Filed: Jul. 7, 2010

(65) Prior Publication Data
US 2011/0009962 A1 Jan. 13, 2011

(30) Foreign Application Priority Data
Jul. 8, 2009 (FR) ...................................... 09 03372

(51) Int. Cl.
*B32B 37/00* (2006.01)
(52) U.S. Cl. ..................... 156/73.1; 156/293; 156/308.2
(58) Field of Classification Search .................... 156/69, 156/73.1, 292, 293, 308.2, 580.1, 580.2
See application file for complete search history.

(56) References Cited

U.S. PATENT DOCUMENTS

| | | | | |
|---|---|---|---|---|
| 4,814,943 A | * | 3/1989 | Okuaki | 361/783 |
| 5,568,684 A | * | 10/1996 | Wong | 29/840 |
| 6,366,206 B1 | | 4/2002 | Ishikawa et al. | |
| 2006/0043178 A1 | | 3/2006 | Tethrake et al. | |

FOREIGN PATENT DOCUMENTS

| | | |
|---|---|---|
| DE | 10328695 A1 | 10/2004 |
| EP | 0334733 A1 | 9/1989 |
| FR | 2697801 A1 | 5/1994 |
| WO | 01/61645 A1 | 8/2001 |
| WO | 2006/115958 A1 | 11/2006 |

OTHER PUBLICATIONS

Search Report of French Application No. 0903372 mailed Feb. 5, 2010.

* cited by examiner

*Primary Examiner* — James Sells
(74) *Attorney, Agent, or Firm* — Lowe Hauptman Berner & Ham

(57) ABSTRACT

One or more embodiments of the invention comprise of a method of integrating an RFID component in an implant or prosthesis substitute or in a surgical instrument. The method comprises at least a step to machine or bore the body of the substitute or of the surgical instrument to form a housing then a cavity intended to receive a cover for the housing. The method further comprises an ultrasonic welding step using a sonotrode to weld the cover to the body of the substitute or of the surgical instrument in polymer or plastic, so that the outer surface of the substitute or of the surgical instrument is bump-free and the weld obtained is sealed and durable. One or more embodiments of the invention also concerns the substitute or surgical instrument.

9 Claims, 4 Drawing Sheets

METHOD TO INTEGRATE AN RFID COMPONENT IN A PROSTHESIS OR IMPLANT SUBSTITUTE OR IN A SURGICAL INSTRUMENT IN POLYMER OR PLASTIC

RELATED APPLICATIONS

The present application is based on, and claims priority from, French Application Number 09/03372, filed Jul. 8, 2009, the disclosure of which is hereby incorporated by reference herein in its entirety.

The present invention concerns the area of prosthesis or implant substitutes or surgical instruments. The present invention more particularly proposes a method to integrate an RFID component in a prosthesis or implant substitute or in a surgical instrument in polymer or plastic, or in the polymer or plastic portion of a prosthesis or implant substitute or of a surgical instrument.

Medical instruments and more particularly prosthesis or implant substitutes and surgical instruments are generally the subject of strict follow-up intended to guarantee their conditions of use, decontamination and patient safety. This follow-up consists of recording and updating all useful data on the instrument, for example its serial number, the clinical history of operated patients, specifications of use and maintenance, dates of these maintenance or sterilisation operations, number of uses, etc. For this purpose, RFID components (Radio Frequency IDentification) which may encompass RFID transponders or tags are widely used since they offer considerable advantages. When joined to an instrument, and associated with a read and/or write module provided with an antenna and central computer, they allow the writing, reading and storing of a large number of data on this instrument. The recording of data can be made automatically during a cleaning operation for example, so as to limit error of human origin. Said operating mode is described for example in document EP 0 992 212 for a metal instrument. Electronic tags are additionally extremely reliable and withstand the high temperatures of sterilisation processes.

In the prior art, the integration of RFID components in metal surgical instruments is therefore well known. However, surgical instrumentation also uses instruments in polymer or plastic which account for about 20% of surgical instruments. In parallel, substitutes of implants or prostheses are members most often in plastic or polymer which are often used as trial components to ensure optimal integration for example of an implant or prosthesis. The surgeon must re-create the environment of the final prosthesis into its intended medium, so that it is properly stabilized and correctly ensures its biomechanical function: the axes, dimensions of the prosthesis inter alia must take into account the tension of ligaments and muscles for good stability of the prosthesis. The surgeon then uses trial components having different characteristics, the most often in polymer or plastic which simulate the final components and their assembly.

As is the case for metal instruments it is similarly necessary to identify the instruments or substitutes in polymer or plastic, so as to identify the size and dimensional properties of the trial component for example which will determine those of the prosthesis. However, on account of its material, the surgical instrument or substitute in polymer or plastic does not allow integration of RFID components using the same techniques as for metal instruments, chiefly to allow maintained sealing and resistance despite successive sterilizations.

The physical properties of polymers or plastics impose constraints which do not exist for metals.

For example, polymers or plastics undergo greater expansion than metals under the effect of heat and they are more sensitive to humidity; which raises problems when sterilizing instruments. As a result, the bonding of a cover onto a housing containing an RFID component, which is a solution for metal instruments, is not an efficient solution. Through expansion of the polymer or plastic and the effect of humidity, the adhesive will undergo constraints making it ineffective and will therefore have an adverse effect on the seal of the housing containing the RFID component which will no longer be functional after ten or so utilizations.

Welding by laser or electron beam is another solution used for metal instruments to fix the cover on the housing. However, plastic has optical properties which prevent efficient welding. The major part of the laser or electron beam is reflected. The remaining part of the beam is not sufficiently effective to weld the cover onto the housing.

It is therefore not possible to repeat the techniques used on metals for polymers or plastics.

The purpose of the present invention is therefore to overcome one or more disadvantages of the prior art, by defining a method to integrate an RFID component in an implant or prosthesis substitute or in a surgical instrument in polymer or plastic.

For this purpose, the invention concerns a method to integrate an RFID component in an implant or prosthesis substitute or in a surgical instrument, which comprises at least:
 a step to machine or bore the body of the substitute or of the surgical instrument to form a housing intended to receive an RFID component;
 a step to machine or bore the body of the substitute or of the surgical instrument to form a cavity intended to receive a cover for the housing;
 a step to place the RFID component in position in the housing;
 a step to place the cover in position in the cavity;
 characterized in that it further comprises:
 an ultrasonic welding step using a sonotrode to weld the cover in polymer or plastic to the body of the implant or prosthesis substitute in polymer or plastic or of the surgical instrument in polymer or plastic, so that the outer surface of the substitute or of the surgical instrument is free of any bumps, and the weld obtained is sealed and durable.

According to another aspect, the diameter of the cover is smaller than the diameter of the cavity.

According to another aspect, the diameter of the cover is equal to or greater than the diameter of the cavity.

According to another aspect, the weld is made between the lower part of the cover and the bottom of the cavity.

According to another aspect, welding is performed between the lower part of the cover and the bottom of the cavity, and between the periphery of the cover and the vertical wall of the cavity.

According to another aspect, during the welding step, the sonotrode is placed astride the cover and the body of the substitute or of the surgical instrument.

According to another aspect, the head of the sonotrode has a smooth or ridged contact surface with the parts of the substitute or surgical instrument to be welded.

According to another aspect, the cover is thicker at its centre than on its periphery, the thickness of the cover decreasing gradually as it approaches its periphery.

According to another aspect, the cover and the body of the substitute or surgical instrument are in the same material or materials having similar viscoelastic and thermal properties.

A further purpose of the invention is achieved by proposing an implant or prosthesis substitute or a surgical instrument comprising a housing formed by machining, intended innerly to receive an RFID component, and a cavity intended for the durable, sealed closing of the housing by a cover, characterized in that the implant or prosthesis substitute or the surgical instrument is in polymer or plastic and in that the cover is welded by ultrasound.

According to another aspect, welding is performed between the lower part of the cover and the bottom of the cavity.

According to another aspect, welding is performed between the lower part of the cover and the bottom of the cavity, and between the periphery of the cover and the vertical wall of the cavity.

The invention will be better understood and other objectives, characteristics, details and advantages thereof will become further apparent from the following explanatory description with reference to the appended figures given as non-limiting examples, in which.

In the remainder hereof, the term <<RFID component>> designates any type of RFID component such as an RFID transponder or tag.

Figure 1A:
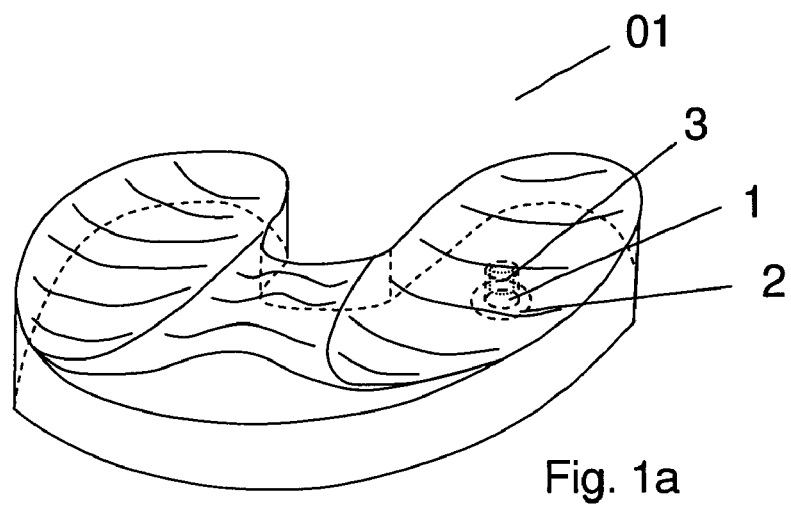
FIG. 1a shows an implant or prosthesis substitute in polymer or plastic which is a trial tibial tray with RFID component integrated according to the invention.
Figure 1B:
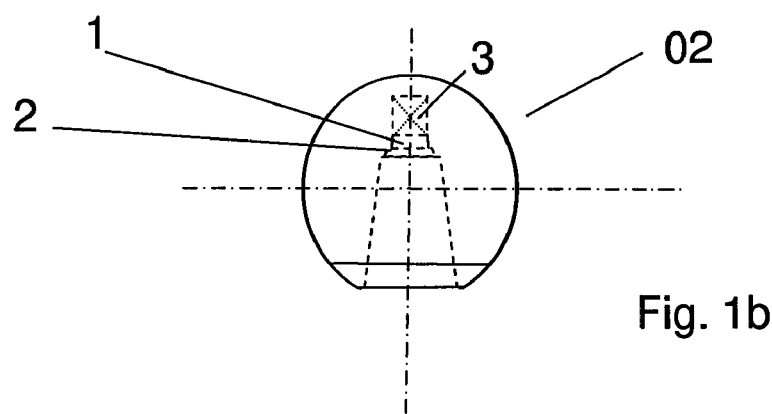
FIG. 1b shows an implant or prosthesis substitute in polymer or plastic which is a trial femoral head with RFID component integrated according to the method of the invention.
Figure 1C:
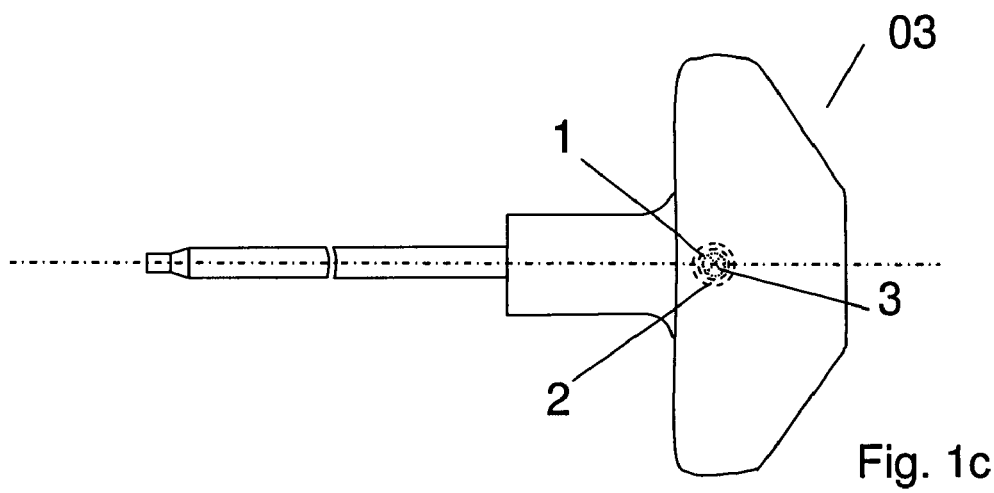
FIG. 1c shows a part in polymer or plastic of a surgical instrument with RFID component integrated according to the method of the invention.
Figure 2B:
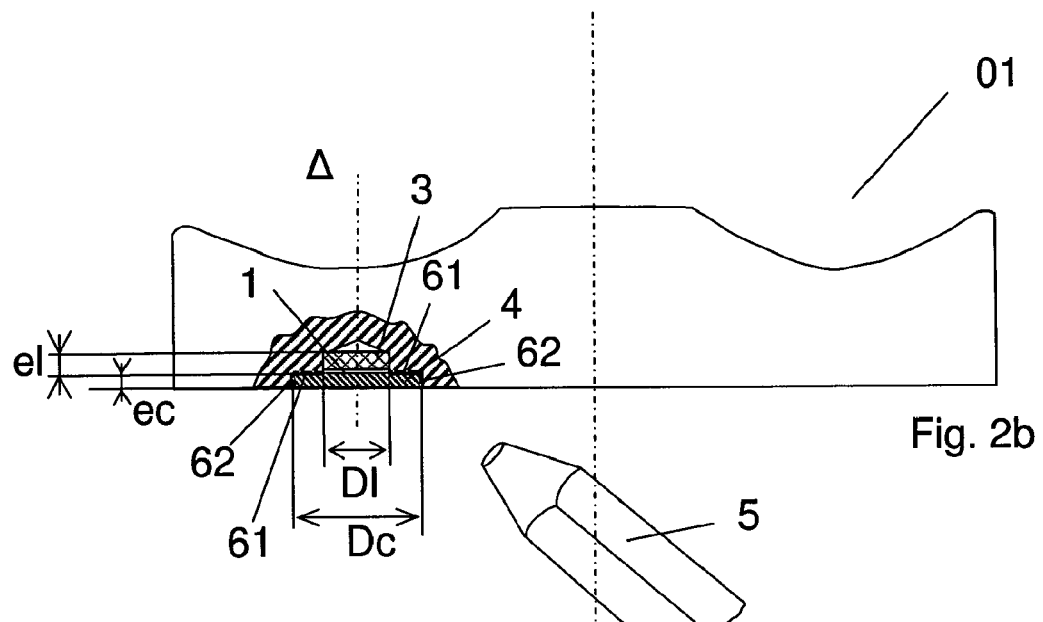
FIG. 2b is front cross-sectional view of the trial tibial tray with the cavity and housing containing the RFID component according to one configuration.
Figure 2A:
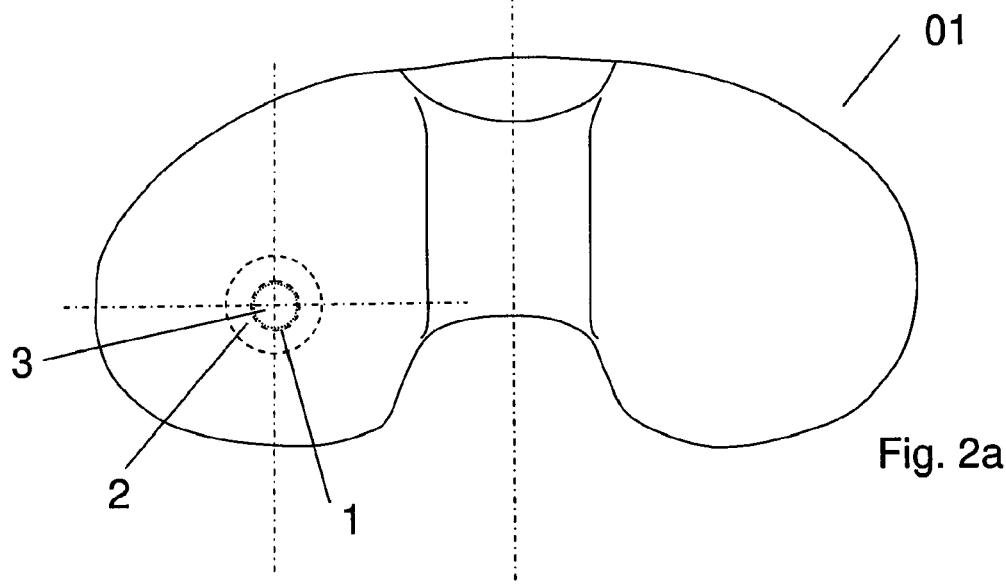
FIG. 2a shows an overhead view of the trial tibial tray with the positioning of the cavity and housing according to one configuration.
Figure 3B:
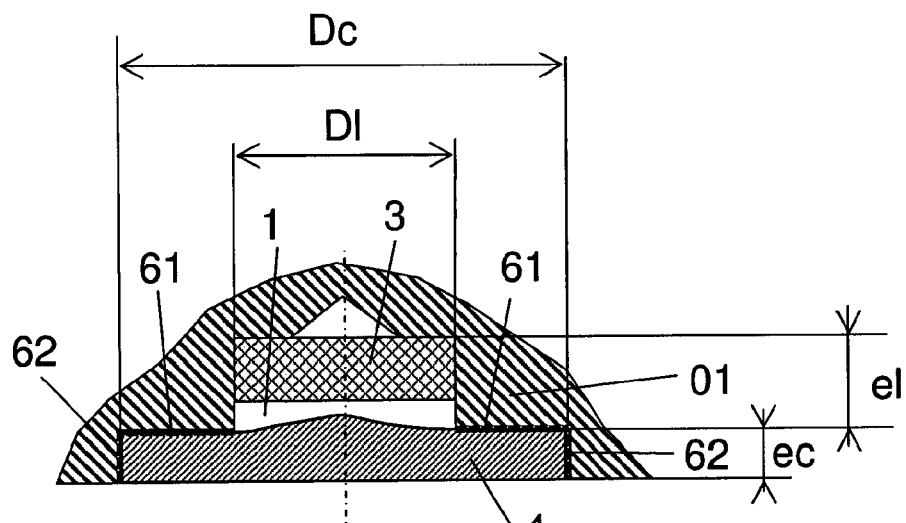
FIG. 3b is a cross-sectional view of the housing and cavity containing the RFID component and closed with a cover.
Figure 3A:
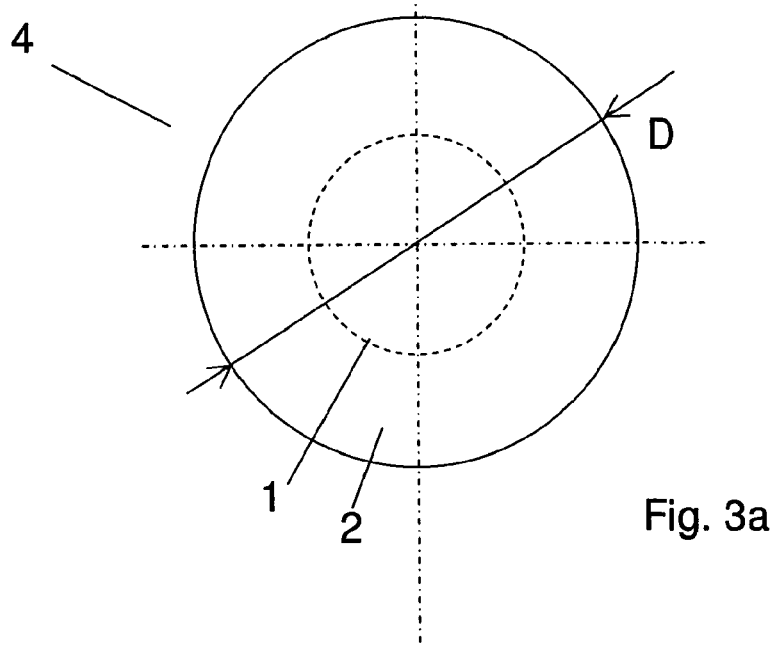
FIG. 3a is an overhead view of the cover.

With reference to the figures, the proposed invention allows the integration of an RFID component 3 in an implant or prosthesis substitute 01, 02 or in a surgical instrument 03 in polymer or plastic. In the remainder of this description, the terms "surgical instrument" and "implant or prosthesis substitute" are to be construed in non-limiting manner. These terms can effectively encompass an implant or prosthesis substitute or a surgical instrument that is entirely in polymer or plastic, or an implant or prosthesis substitute or surgical instrument partly in polymer or plastic. As examples illustrated FIGS. 1a and 1b, the implant or prosthesis substitute may be a trial tibial tray 01 (FIG. 1a) or trial femoral head 02 (FIG. 1b). In FIG. 1c, the surgical instrument may be a manipulating handle 03 in polymer or plastic of a complete surgical instrument. In the remainder of FIGS. 2a and 2b, only the tibial tray 01 is illustrated for reasons of clarity and not of limitation.

In non-limiting manner, the constituent polymers of the implant or prosthesis substitute 01, 02 or of the surgical instrument 03 may be polyacetal (POM), polysulfone (PSU), polyphenylsulfone (PPSU), polyethersulfone (PES), polyphenylene ether (PPE), polyetherimide (PEI), polyetheretherketone (PEEK) or polyetherketoneketone (PEKK).

Figure 4:
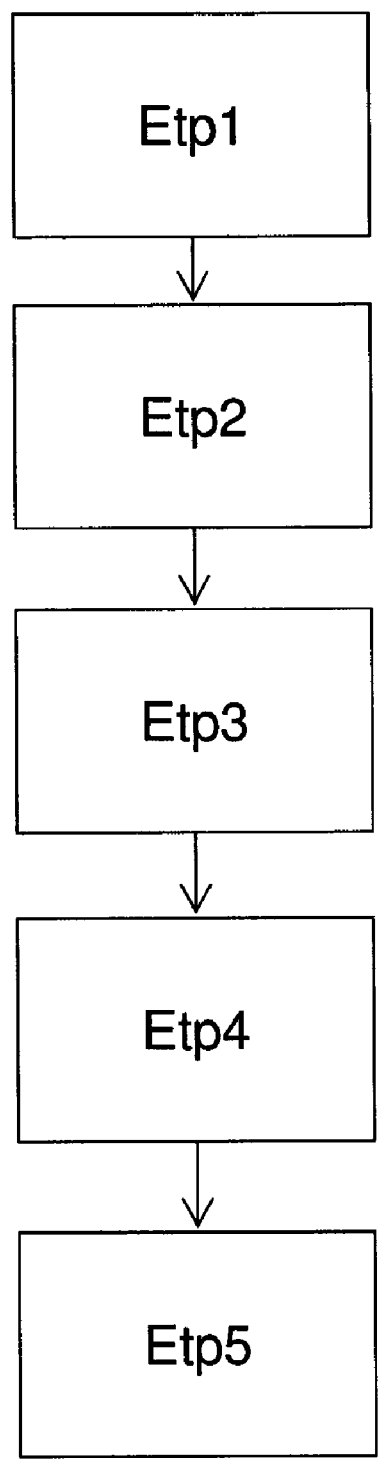
FIG. 4 is a flow chart illustrating the method of the invention.

With reference to FIG. 4, the invention concerns a method to integrate an RFID component 3 in an implant or prosthesis substitute 01, 02 or in a surgical instrument 03 in polymer or plastic which comprises at least the following steps:

A step (Etp1) to machine or bore the body of the implant or prosthesis substitute 01, 02 or of the surgical instrument 03, to form a housing 1 of substantially cylindrical shape intended to receive an RFID component 3.

A following step (Etp2) in which machining or boring is also carried out to form a substantially cylindrical cavity 2 intended to receive the cover 4 closing the housing 1.

The machining and boring operations to form the housing 1 and cavity 2 are performed along an axis Δ perpendicular to the outer surface of the implant or prosthesis substitute 01, 02 or of the surgical instrument 03.

It is to be noted that the bore diameter DI forming the housing 1 is smaller than the diameter Dc of the bore forming the cavity 2 for the cover 4. In addition, the thickness or depth el of the bore forming the housing 1 is greater than the depth ec of the bore forming the cavity 2 for the cover 4.

Depending on the body portion of the implant or prosthesis implant 01, 02 or of the surgical instrument 03 which is machined and on the dimensions of the RFID component 3, the bore to form the housing 1 must be made at a depth el substantially in the vicinity of the outer surface of the body of the implant or prosthesis substitute 01, 02 or of the surgical instrument 03.

The thickness of the cover 4 and the dimensions of the housing 1 allows the RFID component 3 to be positioned substantially in the vicinity of the outer surface of the implant or prosthesis substitute 01, 02 or of the surgical instrument 03, so that the data contained in the RFID component 3 is able to be read by a reader system 5. The thickness of the cover 4 must also allow the reader system 5 to send data to be stored in the RFID component 3. The cover 4 has a thickness which may vary from 0.7 mm to 1.3 mm. Advantageously, the cover 4 has a thickness of 1 mm. The cover 4 has a diameter D which may vary from 9.97 mm to 10.02 mm. Advantageously, the cover 4 has a diameter D of 10 mm.

The cover 4 and the body of the implant or prosthesis substitute 01, 02 or of the surgical instrument 03 are in materials having similar viscoelastic and thermal properties.

Advantageously, the cover 4 and the implant or prosthesis implant 01, 02 or the body of the surgical instrument 03 are in the same material.

In following step (Etp3), the RFID component 3 is placed in the housing 1.

During the next step (Etp4) the cover 4 is placed in position in the cavity 2.

In one configuration, the cover 4 has a smaller diameter D than the diameter Dc of the cavity 2. The resulting clearance between the edges of the cover 4 and the side walls of the cavity 2 does not exceed $\frac{1}{10}$ of a millimeter. Advantageously, the clearance between the edges of the cover 4 and the side walls of the cavity 2 does not exceed $\frac{1}{20}$ of a millimeter.

In another preferred configuration, the cover 4 has a diameter D equal to or greater than the diameter Dc of the cavity 2. The diameter D of the cover 4 does not exceed the diameter Dc of the cavity 2 by more than $\frac{1}{20}$ of a millimeter. Advantageously, the diameter D of the cover 4 does not exceed the diameter Dc of the cavity 2 by more than $\frac{1}{40}$ of a millimeter. Preferably, the diameter D of the cover 4 is equal to the diameter Dc of the cavity 2. In this configuration, the elasticity of the polymer or plastic allows the insertion of the cover 4 in the cavity 2.

In one configuration, and in non-limiting manner, the cavity 2 has a diameter Dc of between 9.98 mm and 10.03 mm and advantageously the diameter Dc of the cavity 2 is 10 mm. In this same configuration, the housing 1 has a diameter DI of 5.6 mm and a thickness or depth el of 2 mm with an RFID component 3 of diameter 5.6 and thickness 1.7 mm.

At the following step (Etp5) the cover 4 is welded to the body of the implant or prosthesis substitute 01, 02 or of the surgical instrument 03 at an ultrasonic welding step (Etp5).

Ultrasonic welding is an industrial technique in which high frequency ultrasound vibrations are applied locally to two parts to be joined together, to create a solid state weld via a pressure field and localized heating. Depending on the setting of the sonotrode, the frequencies used may range from 2 kHz to 40 kHz with amplitudes adapted to the type of polymer or plastic forming the cover 4 and the implant or prosthesis substitute 01, 02 or the surgical instrument 03.

It is to be noted that the sonotrode used for welding may have a smooth, striated or ridged head, the part which comes into contact with the parts to be welded. A sonotrode with ridged or striated head adds to the efficacy of the ultrasound vibrations by mechanical work-hardening. This relief of surface of the sonotrode head allows improvement of the interpenetration of the material(s) of the cover 4 and of the implant or prosthesis substitute 01, 02 or the surgical instrument 03.

The parameters controlling the welding are ultrasound frequency, pressure of the sonotrode head on the parts to be welded, application time of the sonotrode and the shape of the sonotrode.

For example in non-limiting manner, for a body of the implant or prosthesis substitute 01, 02 or of the surgical instrument 03 made of polyacetal, the energy to be applied is 100 J with a frequency of 300 Hz and a pressure stress of 200 N during 2.8 s.

The contact surface of the sonotrode with the area to be welded is preferably annular.

Advantageously, the sonotrode head is placed astride the cover 4 and the body of the implant or prosthesis substitute 01, 02 or of the surgical instrument 03 during the welding step, coming to bear upon the cover 4. When soldering, the sonotrode head then must have a contact surface covering both the peripheral area of the cover 4 and the area around the cavity 2 intended to receive the cover 4 of the body of the implant or prosthesis substitute 01, 02 or of the surgical instrument 03. The sonotrode head is not applied on the whole surface of the cover 4. This sonotrode head configuration allows the elimination of bumps or shoulder between the cover 4 and the body of the implant or prosthesis substitute 01, 02 or of the surgical instrument 03.

In the configuration in which the cover 4 has a smaller diameter D than the diameter Dc of the cavity 2, the weld is created at the contact surfaces 61 of the cover 4 and cavity 2 i.e. on the lower part of the cover 4 and the bottom of the cavity 2.

In the configuration in which the cover 4 has a diameter D equal to or greater than the diameter Dc of the cavity 2, the weld is created at the contact surfaces 61 and 62 of the cover 4 and cavity 2 i.e. between the lower part of the cover 4 and the bottom of the cavity 2 as well as between periphery of the cover 4 and the periphery or vertical wall of the cavity 2. This latter configuration is able to provide optimal sealing of the housing 1. Preferably, there must be then the widest possible contact between the cover 4 and the cavity 2. The difference between the cavity diameter Dc and the housing diameter DI is equal to or greater than 3 mm in order to have optimal contact surface between the lower part of the cover 4 and the bottom of the cavity 2 and then to improve the sealing of the housing 1.

The welds 61, 62 at the contact areas of the cover 4 and cavity 2 of the implant or prosthesis substitute 01, 02 or of the surgical instrument 03 are therefore achieved by local heating, collapse and optionally work-hardening of the materials.

Advantageously, the cover 4 is reinforced at its centre. For this purpose, the thickness of the cover 4 is greater at its centre than on its periphery. The thickness of the cover decreases gradually as it approaches its periphery. This allows more efficient welding of the cover 4 in the cavity 2. In non limiting manner, the cover 4 has a thickness increased of 0.5 mm in its centre in comparison with the thickness in its peripheral zone.

With this method, it is possible to obtain an implant or prosthesis substitute 01, 02 in polymer or plastic, or a surgical instrument 03 in polymer or plastic comprising a housing 1 formed by machining and intended innerly to receive an RFID component 3, and a cavity 2 intended to close the housing 1 in sealed and durable manner by a cover 4 in polymer or plastic welded by ultrasound to the body of the implant or prosthesis substitute 01, 02 or of the surgical instrument 03.

It will be obvious to the person skilled in the art that the present invention permits embodiments in numerous other specific forms without departing from the scope of application of the invention as claimed. Therefore, the described embodiments are to be construed as illustrations which may be modified in the field defined by the scope of the appended claims, and the invention is not to be limited to the aforementioned details.

The invention claimed is:

1. A method of integrating an RFID component in an implant or prosthesis substitute or in a surgical instrument comprising at least:
   a step (Etp1) to machine or bore the body of the implant or prosthesis substitute or of the surgical instrument to form a housing intended to receive an RFID component;
   a step (Etp2) to machine or bore the body of the implant or prosthesis substitute or of the surgical instrument to form a cavity intended to receive a cover for the housing;
   a step (Etp3) to place the RFID component in position in the housing;
   a step (Etp4) to place the cover in the cavity; and
   an ultrasonic welding step (Etp5) using a sonotrode to weld the cover in polymer or plastic to the body of the implant or prosthesis substitute in polymer or plastic or of the surgical instrument, so that the outer surface of the implant or prosthesis substitute or of the surgical instrument is free of any bumps or shoulder between the cover and the body of the implant or prosthesis substitute or of the surgical instrument and the weld obtained is sealed and durable.

2. The method according to claim 1, the diameter of the cover being smaller than the diameter of the cavity.

3. The method according to claim 1, the diameter of the cover being equal to or greater than the diameter of the cavity.

4. The method according claim 1, the weld being made between the lower part of the cover and the bottom of the cavity.

5. The method according to claim 1, the weld being made between the lower part of the cover and the bottom of the cavity and between the periphery of the cover and the vertical wall of the cavity.

6. The method according to claim 1, wherein at welding step (Etp5) the sonotrode is placed astride the cover and the body of the implant or prosthesis substitute or of the surgical instrument so that the sonotrode head have a contact surface covering both the peripheral area of the cover and the area around the cavity intended to receive the cover of the body of the implant or prosthesis substitute or of the surgical instrument.

7. The method according to claim 1, the head of the sonotrode having a smooth or ridged contact surface with the parts of the implant or prosthesis substitute or of the surgical instrument to be welded.

8. The method according to claim 1, the cover being thicker at the centre than on the periphery, the thickness of the cover decreasing gradually toward the periphery.

9. The method according to claim 1, the cover and the body of the implant or prosthesis substitute or of the surgical instrument being in the same material or materials having similar viscoelastic properties.

\* \* \* \* \*